United States Patent
Thompson

(10) Patent No.: US 9,642,728 B2
(45) Date of Patent: *May 9, 2017

(54) STENT WITH ENHANCED FRICTION

(71) Applicant: Covidien LP, Mansfield, MA (US)

(72) Inventor: Paul Thompson, Minnetonka, MN (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/688,576

(22) Filed: Apr. 16, 2015

(65) Prior Publication Data

US 2015/0282956 A1   Oct. 8, 2015

Related U.S. Application Data

(63) Continuation of application No. 13/535,413, filed on Jun. 28, 2012, now Pat. No. 9,011,518, which is a
(Continued)

(51) Int. Cl.
*A61F 2/82* (2013.01)
*A61F 2/91* (2013.01)
(Continued)

(52) U.S. Cl.
CPC .................. *A61F 2/82* (2013.01); *A61F 2/91* (2013.01); *A61F 2/915* (2013.01); *A61F 2/95* (2013.01);
(Continued)

(58) Field of Classification Search
CPC ...... A61F 2220/0025; A61F 2220/0033; A61F 2220/0083; A61F 2250/0021;
(Continued)

(56) References Cited

U.S. PATENT DOCUMENTS 4,101,984 A   7/1978   MacGregor
4,733,665 A   3/1988   Palmaz
(Continued)

FOREIGN PATENT DOCUMENTS

DE   19722384 A1   12/1998
EP   0688545 A1   12/1995
(Continued)

OTHER PUBLICATIONS

Dunitz, Excerpts from "Handbook of Coronary Stents," Rotterdam Thoraxcentre Group, University Hospital Dijkzigt, Rotterdam, The Netherlands, 1997, 23 pages.
(Continued)

*Primary Examiner* — Christian Sevilla
*Assistant Examiner* — Cheryl Miller

(57) ABSTRACT

A stent for placement in a body lumen is fabricated by forming a tube having an undeployed diameter sized for the tube to be placed on a deployment balloon and advanced through a body lumen to a deployment site. The tube is expandable upon inflation of the balloon to an enlarged diameter sized for the tube to be retained within the lumen at the site upon deflation and withdrawal of the balloon. The tube has a stent axis extending between first and second axial ends of the tube. The tube has an exterior surface and an interior surface. The tube is polished to polish the exterior surface to a smooth surface finish and with at least a portion of the interior surface having a rough surface finish rougher than the surface finish of the exterior surface.

16 Claims, 2 Drawing Sheets

Related U.S. Application Data continuation of application No. 10/896,533, filed on Jul. 22, 2004, now Pat. No. 8,236,047, which is a continuation of application No. 09/879,425, filed on Jun. 12, 2001, now Pat. No. 6,827,732, which is a continuation of application No. 09/404,418, filed on Sep. 23, 1999, now Pat. No. 6,254,631.

(51) Int. Cl.
*A61F 2/915* (2013.01)
*A61F 2/95* (2013.01)
*A61F 2/958* (2013.01)
*A61F 2/86* (2013.01)

(52) U.S. Cl.
CPC ............ *A61F 2/86* (2013.01); *A61F 2/958* (2013.01); *A61F 2002/91541* (2013.01); *A61F 2002/91558* (2013.01); *A61F 2002/9522* (2013.01); *A61F 2002/9583* (2013.01); *A61F 2230/0013* (2013.01); *A61F 2230/0063* (2013.01); *A61F 2230/0069* (2013.01); *A61F 2240/001* (2013.01); *A61F 2250/0025* (2013.01); *Y10S 623/901* (2013.01); *Y10S 623/921* (2013.01)

(58) Field of Classification Search
CPC ...... A61F 2250/0025; A61F 2250/0023; A61F 2250/0024
See application file for complete search history.

(56) References Cited

U.S. PATENT DOCUMENTS

| | | | | |
|---|---|---|---|---|
| 4,739,762 | A | 4/1988 | Palmaz | |
| 4,767,418 | A * | 8/1988 | Deininger | A61F 2/0077 623/1.39 |
| 4,776,337 | A | 10/1988 | Palmaz | |
| 4,869,259 | A | 9/1989 | Elkins | |
| 5,019,085 | A | 5/1991 | Hillstead | |
| 5,084,064 | A | 1/1992 | Barak et al. | |
| 5,195,984 | A | 3/1993 | Schatz | |
| 5,342,348 | A | 8/1994 | Kaplan | |
| 5,419,760 | A | 5/1995 | Narciso, Jr. | |
| 5,421,955 | A | 6/1995 | Lau et al. | |
| 5,423,885 | A * | 6/1995 | Williams | A61F 2/92 606/194 |
| 5,443,500 | A | 8/1995 | Sigwart | |
| 5,449,373 | A | 9/1995 | Pinchasik et al. | |
| 5,476,508 | A | 12/1995 | Amstrup | |
| 5,514,154 | A | 5/1996 | Lau et al. | |
| 5,540,712 | A | 7/1996 | Kleshinski et al. | |
| 5,569,295 | A | 10/1996 | Lam | |
| 5,591,197 | A | 1/1997 | Orth et al. | |
| 5,607,480 | A | 3/1997 | Beaty | |
| 5,649,977 | A | 7/1997 | Campbell | |
| 5,682,946 | A | 11/1997 | Schmidt et al. | |
| 5,695,516 | A | 12/1997 | Fischell et al. | |
| 5,697,971 | A | 12/1997 | Fischell et al. | |
| 5,707,386 | A | 1/1998 | Schnepp-Pesch et al. | |
| 5,707,387 | A | 1/1998 | Wijay | |
| 5,718,713 | A | 2/1998 | Frantzen | |
| 5,723,004 | A * | 3/1998 | Dereume | A61F 2/07 623/1.35 |
| 5,725,572 | A | 3/1998 | Lam et al. | |
| 5,728,131 | A | 3/1998 | Frantzen et al. | |
| 5,741,327 | A | 4/1998 | Frantzen | |
| 5,746,272 | A * | 5/1998 | Mastrorio | A61F 2/30771 164/35 |
| 5,746,745 | A * | 5/1998 | Abele | A61F 2/958 604/103.08 |
| 5,762,631 | A | 6/1998 | Klein | |
| 5,769,884 | A * | 6/1998 | Solovay | A61F 2/07 606/194 |
| 5,788,558 | A | 8/1998 | Klein | |
| 5,800,526 | A | 9/1998 | Anderson et al. | |
| 5,810,872 | A | 9/1998 | Kanesaka et al. | |
| 5,826,586 | A * | 10/1998 | Mishra | A61F 2/30767 128/898 |
| 5,837,313 | A * | 11/1998 | Ding | A61F 2/82 427/2.21 |
| 5,843,172 | A | 12/1998 | Yan | |
| 5,853,419 | A | 12/1998 | Imran | |
| 5,888,201 | A | 3/1999 | Stinson et al. | |
| 5,910,170 | A * | 6/1999 | Reimink | A61F 2/2418 623/2.38 |
| 5,928,280 | A | 7/1999 | Hansen et al. | |
| 5,972,027 | A | 10/1999 | Johnson | |
| 5,980,566 | A | 11/1999 | Alt et al. | |
| 6,063,092 | A | 5/2000 | Shin | |
| 6,071,305 | A | 6/2000 | Brown et al. | |
| 6,096,052 | A | 8/2000 | Callister et al. | |
| 6,120,535 | A * | 9/2000 | McDonald | A61F 2/92 623/1.39 |
| 6,190,404 | B1 * | 2/2001 | Palmaz | A61F 2/91 623/1.15 |
| 6,217,607 | B1 | 4/2001 | Alt | |
| 6,245,104 | B1 | 6/2001 | Alt | |
| 6,254,631 | B1 * | 7/2001 | Thompson | A61F 2/82 623/1.11 |
| 6,258,115 | B1 * | 7/2001 | Dubrul | A61B 17/12109 606/191 |
| 6,261,320 | B1 | 7/2001 | Tam et al. | |
| 6,478,815 | B1 | 11/2002 | Alt | |
| 6,537,202 | B1 | 3/2003 | Frantzen | |
| 6,573,311 | B1 * | 6/2003 | Martakos | A61F 2/06 264/423 |
| 6,689,043 | B1 | 2/2004 | McIntire et al. | |
| 6,827,732 | B2 * | 12/2004 | Thompson | A61F 2/82 623/1.15 |
| 6,979,346 | B1 * | 12/2005 | Hossainy | A61F 2/91 623/1.11 |
| 7,398,780 | B2 | 7/2008 | Callister et al. | |
| 8,236,047 | B2 | 8/2012 | Thompson | |
| 9,011,518 | B2 * | 4/2015 | Thompson | A61F 2/82 623/1.39 |
| 2001/0039395 | A1 | 11/2001 | Mareiro et al. | |
| 2002/0016623 | A1 * | 2/2002 | Kula | A61F 2/91 623/1.11 |
| 2002/0049492 | A1 | 4/2002 | Lashinski et al. | |
| 2003/0004535 | A1 | 1/2003 | Musbach et al. | |
| 2007/0151093 | A1 | 7/2007 | Curcio et al. | |

FOREIGN PATENT DOCUMENTS

| | | |
|---|---|---|
| EP | 0701803 A1 | 3/1996 |
| EP | 0709067 A2 | 5/1996 |
| EP | 0732088 A2 | 9/1996 |
| EP | 0800800 A1 | 10/1997 |
| EP | 0850604 A2 | 7/1998 |
| FR | 2764794 | 12/1998 |
| WO | 9949810 | 10/1999 |
| WO | 9952471 | 10/1999 |

OTHER PUBLICATIONS

Prosecution History from U.S. Pat. No. 6,827,732, dated Jun. 12, 2001 through Jul. 16, 2004, 122 pages.

Prosecution History from U.S. Pat. No. 8,236,047, dated Mar. 6, 2008 through Apr. 2, 2012, 65 pages.

Prosecution History from U.S. Pat. No. 9,011,518, dated Jun. 28, 2012 through Mar. 25, 2015, 108 pages.

* cited by examiner

_US 9,642,728 B2_

STENT WITH ENHANCED FRICTION

This application is a continuation of U.S. patent application Ser. No. 13/535,413 by Paul J. Thompson, which was filed on Jun. 28, 2012 and will issue as U.S. Pat. No. 9,011,518 on Apr. 21, 2015, which is a continuation of U.S. patent application Ser. No. 10/896,533, which was filed Jul. 22, 2004 and issued as U.S. Pat. No. 8,236,047 on Aug. 7, 2012, which is a continuation of U.S. patent application Ser. No. 09/879,425, which was filed on Jun. 12, 2001 and issued as U.S. Pat. No. 6,827,732 on Dec. 7, 2004, which is a continuation of U.S. patent application Ser. No. 09/404,418, which was filed on Sep. 23, 1999 and issued as U.S. Pat. No. 6,254,631 on Jul. 3, 2011, each of which is incorporated herein by reference in its entirety.

BACKGROUND OF THE INVENTION

1. Field of the Invention

This invention pertains to stents for use in intraluminal applications. More particularly, this invention pertains to a stent with enhanced friction on a delivery catheter.

2. Description of the Prior Art

Stents are widely used for numerous applications where the stent is placed in the lumen of a patient and expanded. Such stents may be used in coronary or other vasculature, as well as other body lumens.

Commonly, stents are cylindrical members. The stents expand from reduced diameters to enlarged diameters. Frequently, such stents are placed on a balloon catheter with the stent in the reduced-diameter state. So placed, the stent is advanced on the catheter to a placement site. At the site, the balloon is inflated to expand the stent to the enlarged diameter. The balloon is deflated and removed, leaving the enlarged diameter stent in place. So used, such stents are used to expand occluded sites within a patient's vasculature or other lumen.

Examples of prior art stents are numerous. For example, U.S. Pat. No. 5,449,373 to Pinchasik et al. teaches a stent with at least two rigid segments joined by a flexible connector. U.S. Pat. No. 5,695,516 to Fischell teaches a stent with a cell having a butterfly shape when the stent is in a reduced-diameter state. Upon expansion of the stent, the cell assumes a hexagonal shape.

To deliver a stent, the stent in a reduced diameter shape is placed surrounding a deflated tip of a balloon catheter. The catheter and stent are simultaneously advanced through a sheath to a deployment site in a body lumen. At the site, the balloon is inflated to expand the stent. Following such expansion, the balloon is deflated. The catheter is withdrawn leaving the expanded stent in place.

In order to prevent the presence of sharp corners and burrs which might otherwise damage a balloon, stents are highly polished to a mirror finish. Unfortunately, a highly polished stent can slip off a balloon tip catheter. Also, when a balloon is inflated, the axially spaced ends of the balloon tend to inflate faster than the center of the balloon. This can result in a concave cross-section (when viewed from the side) in the balloon and stent at a point in time prior to full expansion of the stent. During this period, ends of the stent may slide toward one another on the balloon toward the center of the balloon resulting in an undesirable compression of the length of the stent.

SUMMARY OF THE INVENTION

According to a preferred embodiment of the present invention, a stent for placement in a body lumen is fabricated by forming a tube having an un-deployed diameter sized for the tube to be placed on a deployment balloon and advanced through a body lumen to a deployment site. The tube is expandable upon inflation of the balloon to an enlarged diameter sized for the tube to be retained within the lumen at the site upon deflation and withdrawal of the balloon. The tube has a stent axis extending between first and second axial ends of the tube. The tube has an exterior surface and an interior surface. The tube is polished to polish the exterior surface to a smooth surface finish and with at least a portion of the interior surface having a rough surface finish rougher than the surface finish of the exterior surface.

DESCRIPTION OF THE PREFERRED EMBODIMENT

Referring now to the several drawing figures in which identical elements are numbered identically, a description of the preferred embodiment of the present invention will now be provided. Where several embodiments are shown, common elements are similarly numbered and not separately described with the addition of apostrophes to distinguish the embodiments.

Figure 1:
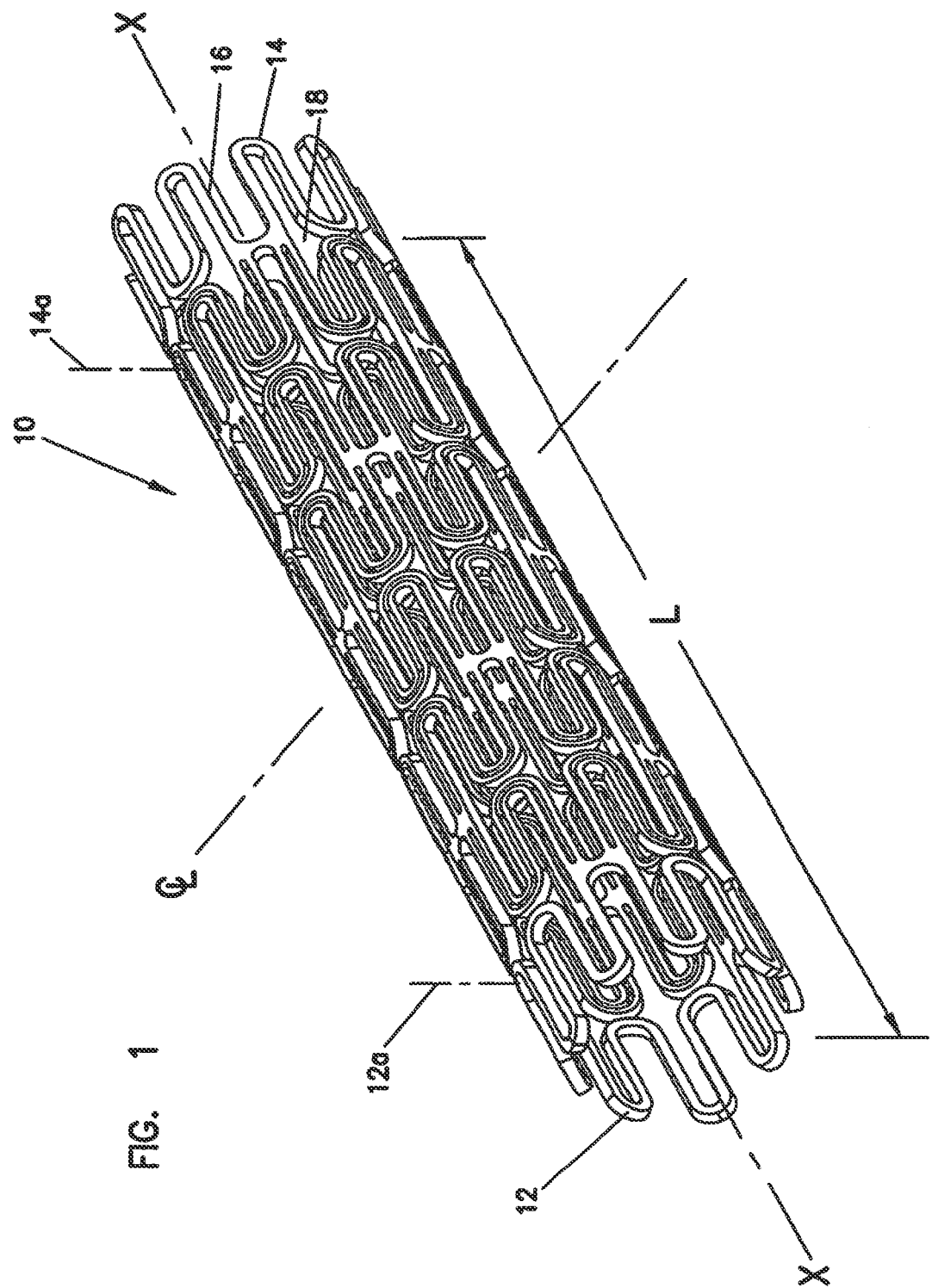
FIG. 1 is perspective view of a stent.

In FIG. 1, a stent 10 is shown. The stent 10 is a hollow reticulated tube having an axis X-X and extending between first and second ends 12, 14. The stent 10 is shown in a reduced diameter state sized to be advanced through a human body lumen to a deployment site in the lumen. By way of non-limiting representative example, the stent may have an axial length L of about 9 mm-76 mm depending on the intended use of the stent (e.g., for opening an occluded site in a coronary artery or other body lumen). By way of none limiting representative example, such a stent 10 may have a reduced or unexpanded diameter D of 2.0 mm and be expandable to an expanded diameter of 10 mm.

Figure 3:
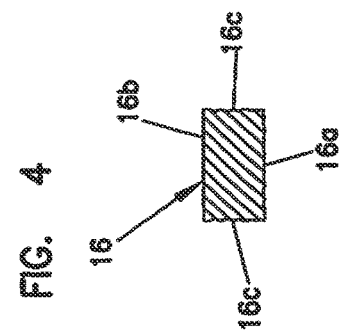
FIG. 3 is a cross-sectional view of a rib of the stent of FIG. 1 before treatment according to the present invention.
Figure 4:
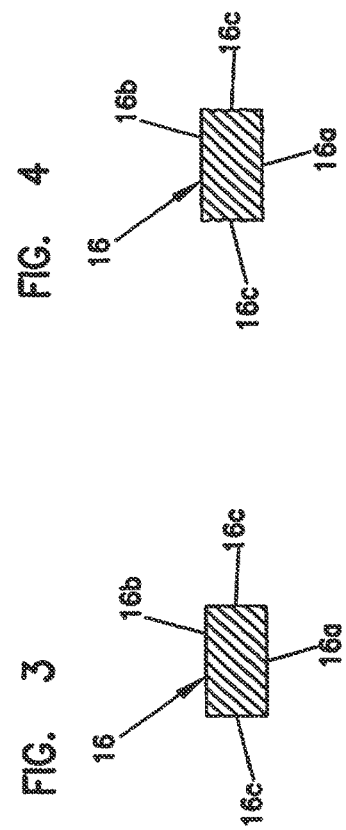
FIG. 4 is the view of FIG. 3 following treatment according to the present invention.

For purposes of illustration, the present invention is described with reference to a stent 10 having a structure such as more fully described in commonly assigned U.S. Pat. Nos. 6,132,460 and 6,132,461. Such a stent 10 is formed from a hollow, solid wall tube of stent material (e.g., titanium, Nitinol, stainless steel etc.). Excess material of the tube is removed through any suitable means such as laser cutting or chemical etching. Removal of the excess material leaves a stent 10 having a plurality of ribs 16 defining a plurality of open cells 18 extending through the wall thickness of the stent 10. The ribs 16 have interior surfaces 16a (FIGS. 3 and 4) facing the axis X-X and exterior surfaces 16b facing away from the axis X-X. The interior and exterior surfaces 16a, 16b are joined by radial surfaces 16c.

In use, the reduced diameter stent 10 is placed on a balloon-tipped catheter. During such placement, the catheter balloon is deflated and the stent 10 is surrounding the balloon. The catheter and mounted stent are passed through the patient's lumen. Commonly, the catheter and stent are advanced through a catheter sheath pre-positioned within the lumen. The catheter and stent are advanced through an open distal end of the sheath to the deployment site within the lumen. At this point, the balloon is inflated to expand the stent 10 to the expanded diameter. After such expansion, the balloon is deflated and the catheter is withdrawn leaving the expanded stent 10 positioned within the lumen.

It will be appreciated that the foregoing description of stent 10 and its placement using a balloon-tipped catheter are previously known. Such description is provided to clarify the benefits of the present invention.

When forming a stent 10 from a solid wall tube as described, surface imperfections may be formed on the stent 10. For example, these can include sharp edges between surfaces 16a and 16c or surfaces 16b and 16c. Further, such imperfections may include burrs. Such imperfections are undesirable. A sharp surface imperfection at the interior surface 16a can damage a catheter balloon thereby degrading or precluding its desired performance. A surface imperfection on the exterior surface 16b can cause the stent 10 to be difficult to advance through a catheter sheath to the desired deployment site.

Recognizing the undesirability of such surface imperfections, the prior art uses polishing techniques to polish a stent 10 to a high degree of smooth surface finish for all of surfaces 16a, 16b and 16c. Unfortunately, such a highly polished stent 10 presents additional problems. Namely, the exterior surfaces of catheter balloons are slippery relative to the material of a highly polished stent 10. Therefore, a stent 10 can be displaced on or fall off a catheter balloon. Also, when a balloon is inflated, the axially spaced ends of the balloon tend to inflate faster than the center of the balloon. This can result in a concave cross-section (when viewed from the side) in the balloon. Since the highly polished stent 10 is slidable on the balloon, the ends 12, 14 of the stent 10 may tend to slide toward one another when the balloon is in the intermediate concave state. Such movement can result in an undesirable compression of the length L of a highly polished stent 10.

The prior art has suggested the use of so-called "sticky" balloon which are coated or otherwise formed with a material having an enhanced adhesion with a highly polished inner surface 16a of a stent 10. However, such balloons are difficult and expensive to manufacture.

The present invention selectively roughens the interior surface 16a of the stent 10 to enhance friction between the stent 10 and a catheter balloon. Such a roughening is counter-intuitive since conventional stent construction theory calls for a smooth, highly polished stent to avoid or minimize raised areas which might otherwise provide sites for thrombus formation or platelet activation after the stent is deployed. However, test data have indicated that a stent 10 with roughened surfaces as will be described does not exhibit excessive thrombus formation or platelet activation.

The interior surface 16a of the stent 10 is roughened to a rough surface finish rougher than the surface finish of the exterior surface 16b. In the roughening process as will be described, the radial surfaces 16c are also roughened.

In a preferred embodiment, only a limited area between ends 12, 14 of the interior surface 16a is roughened. This area is shown in FIG. 1 as bounded between lines 12a, 14a spaced about 4 mm into the interior of the stent 10 from ends 12, 14. The roughened area completely surrounds the axis X-X. While the entire interior surface 16a could be roughened, it is preferred that at least areas on opposite sides of a center-line CL of the stent 10 be roughened to prevent axial shortening of the stent. Preferably, the boundaries 12a, 14a of the roughened area are as close as possible to ends 12, 14 to prevent even a small amount of axial shortening.

Figure 2:
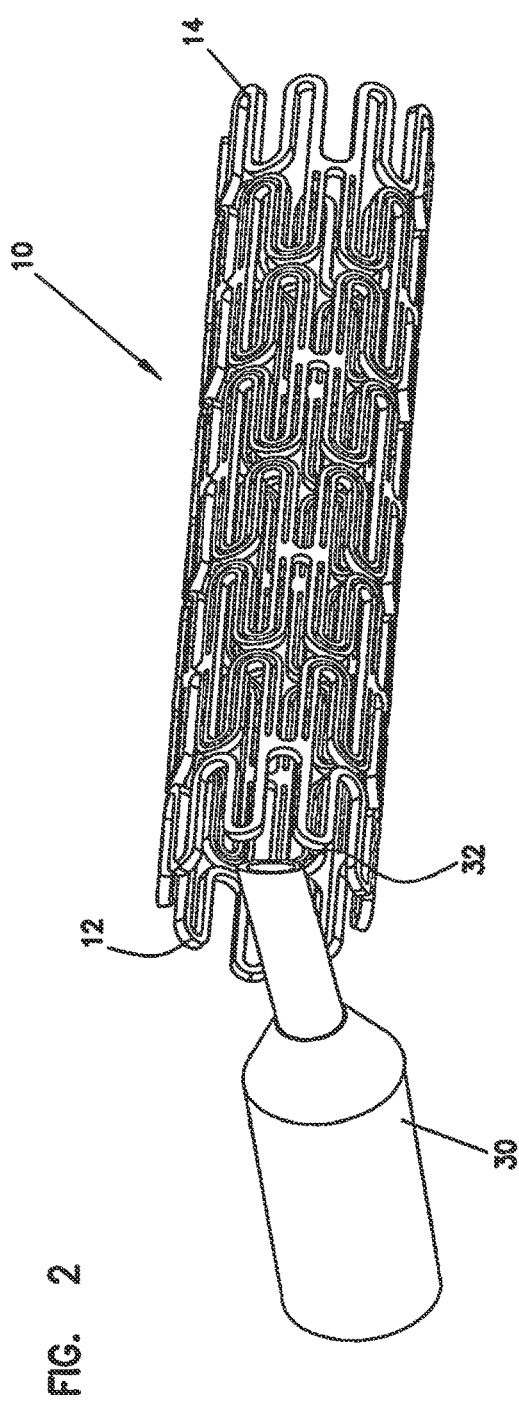
FIG. 2 is the view of FIG. 1 with a nozzle poised to spray a particulate matter against the interior of the stent according to the present invention.

As shown in FIG. 2, the roughening is provided by a nozzle 30 positioned adjacent an end (e.g., end 12) of the stent 10. The nozzle 30 is positioned with a nozzle orifice 32 directing a particulate stream at an angle relative to the stent axis X-X. In a preferred embodiment, the orifice is positioned 1.0 mm from end 12 and the angle is 30°. By way of example, the nozzle 30 is a product sold under the name "Microblaster" of Comco, Inc. and has an orifice diameter of 0.015 inch. The particulate stream is powder silicon carbide size of about SO micron which is discharged from the orifice at a pressure of 60 psi. During the application of the particulate stream, the stent 10 is rotated 360° about its axis X-X. When it is desirable to limit the axial length of the roughened area, a rod (not shown) may be inserted through the opposite end 14 of the stent 10 to expose only the area 12 to be roughened. Following roughening through end 12, the procedure is repeated on the opposite end 14 to uniformly roughen the surface 16a. If desired, a tube may be placed around the exterior surface 16b to insure the exterior surface 16b is not roughened by the process. In the roughening process, the radial surfaces 16c are also roughened. Roughening of the radial surfaces 16c is not essential to the present invention. However, such roughening is not detrimental.

The surfaces 16a, 16c are uniformly covered with pits which are approximately 3 to 20 microns in size.

With a stent 10 as described, the stent 10 has enhanced friction on a deployment balloon. Slippage of the stent 10 on the balloon is reduced and integrity of the axial length L of the stent 10 is maintained. Also, and surprisingly, the stent 10 performs without undue thrombus formation or platelet activation in the roughened area of surface 16b.

From the foregoing, the present invention has been shown in a preferred embodiment. Modifications and equivalents are intended to be included within the scope of the appended claims.

What is claimed is:

1. An intravascular device comprising:
    a tubular stent body expandable from an undeployed configuration to a deployed configuration, the stent body defining an exterior surface and an interior surface arranged about a stent axis, wherein some areas of the interior surface have a roughened surface finish and other areas of the interior surface are devoid of the roughened surface finish, the some areas having the roughened surface finish being on opposite sides of a center line of the stent body, the center line being orthogonal to the stent axis,
    wherein substantially all of the exterior surface of the stent body has a generally smooth finish relative to the roughened surface finish of the interior surface,
    wherein the stent body includes a plurality of ribs defining openings extending through the stent body from the interior surface to the exterior surface, and
    wherein the roughened surface finish of the interior surface defines pits having a maximum dimension of approximately 3 microns to approximately 20 microns in size.

2. The intravascular device of claim 1, the ribs having radial surfaces extending from the interior surface to the exterior surface, wherein the radial surfaces have the roughened surface finish.

3. The intravascular device of claim 1, wherein the roughened surface finish extends along the stent axis and is spaced from axial ends of the stent body such that axial end segments of the interior surface are devoid of the roughened surface finish and a central segment between the axial end segments has the roughened surface finish.

4. The intravascular device of claim 1, wherein the some areas having the roughened surface finish surround the stent axis.

5. The intravascular device of claim 1, wherein the stent body is formed from metal.

6. The intravascular device of claim 1, wherein the exterior surface is polished to a smooth surface finish.

7. The intravascular device of claim 1, wherein the stent body is formed from titanium, Nitinol, or stainless steel.

8. A system comprising:
a catheter comprising a balloon;
a stent placed on the catheter surrounding the balloon, the stent comprising:
   a stent body expandable from an undeployed configuration to a deployed configuration, the stent body defining an exterior surface and an interior surface arranged about a stent axis, wherein some areas of the interior surface have a roughened surface finish and other areas of the interior surface are devoid of the roughened surface finish, the some areas having the roughened surface finish being on opposite sides of a center line of the stent body, the center line being orthogonal to the stent axis,
   wherein substantially all of the exterior surface of the stent body has a generally smooth finish relative to the roughened surface finish of the interior surface,
   wherein the stent body includes a plurality of ribs defining openings extending through the stent body from the interior surface to the exterior surface, wherein
      the roughened surface finish of the interior surface defines pits having a maximum dimension of approximately 3 microns to approximately 20 microns in size, and wherein
wherein the balloon is configured to be inflated to expand the stent to the deployed configuration.

9. The system of claim 8, wherein the roughened surface finish extends along the stent axis and is spaced from axial ends of the stent body such that axial end segments of the interior surface are devoid of the roughened surface finish and a central segment between the axial end segments has the roughened surface finish.

10. A method comprising:
creating a roughened surface finish for some areas of an interior surface of a tubular stent body, the stent body being expandable from an undeployed configuration to a deployed configuration, and defining an exterior surface and the interior surface arranged about a stent axis,
wherein some areas of the interior surface have the roughened surface finish and other areas of the interior surface are devoid of the roughened surface finish, the some areas having the roughened surface finish being on opposite sides of a center line of the stent body, the center line being orthogonal to the stent axis, wherein substantially all of the exterior surface of the stent body has a generally smooth finish relative to the roughened surface finish,
wherein the stent body includes a plurality of ribs defining openings extending through the stent body from the interior surface to the exterior surface, and
wherein creating the roughened surface finish comprises defining pits having a maximum dimension of approximately 3 microns to approximately 20 microns in size in the interior surface.

11. The method of claim 10, wherein creating the roughened surface finish comprises directing a particulate stream at the interior surface of the stent body at an angle relative to the stent axis.

12. The method of claim 11, wherein directing the particulate stream at the interior surface of the stent body comprises positioning a nozzle adjacent an end of the stent body, wherein the particulate stream exits the nozzle.

13. The method of claim 12, wherein the end is a first end, the method further comprising inserting a rod through a second end of the stent body to expose only the some areas.

14. The method of claim 11, further comprising rotating the stent body about the stent axis while directing the particulate stream at the interior surface of the stent body.

15. The method of claim 11, wherein the particulate stream comprises powder silicon carbide.

16. The method of claim 11, further comprising polishing the exterior surface of the stent body.

* * * * *